United States Patent [19]

Shiu

[11] Patent Number: 5,478,326
[45] Date of Patent: Dec. 26, 1995

[54] ARTERIAL DEVICE FOR CONTROL OF BLEEDING FROM A PUNCTURE IN AN ARTERY WALL

[76] Inventor: Man F. Shiu, Cardiovascular Innovations Consultancy, 39 Dyott Road, Moseley, Birmingham B13 9QZ, United Kingdom

[21] Appl. No.: 246,314

[22] Filed: May 18, 1994

Related U.S. Application Data

[63] Continuation-in-part of Ser. No. 989,053, Dec. 10, 1992, abandoned.

[51] Int. Cl.⁶ ............................................. A61M 5/32
[52] U.S. Cl. ............................................. 604/264
[58] Field of Search ........................ 604/112, 158, 604/162, 163, 164, 171, 174, 177, 180, 264, 280, 248, 256

[56] References Cited

U.S. PATENT DOCUMENTS

| | | | |
|---|---|---|---|
| 3,094,124 | 6/1963 | Birtwell | 604/280 |
| 4,230,110 | 10/1980 | Beroff | 604/280 |
| 4,392,853 | 7/1983 | Muto | 604/171 |
| 4,700,694 | 10/1987 | Shishido | 604/158 |
| 4,723,939 | 2/1988 | Anaise | 604/96 |
| 4,725,267 | 2/1988 | Vaillancourt | 604/192 |
| 4,738,658 | 4/1988 | Magro et al. | 604/158 |
| 4,787,882 | 11/1988 | Clarin | 604/264 |
| 5,074,846 | 12/1991 | Clegg et al. | 604/158 |
| 5,106,376 | 4/1992 | Moonen et al. | 604/158 |
| 5,112,310 | 5/1992 | Grobe | 604/164 |
| 5,267,972 | 12/1993 | Lombart | 604/192 |
| 5,269,765 | 12/1993 | Kuracina | 604/192 |
| 5,290,254 | 3/1994 | Vaillancourt | 604/192 |
| 5,295,972 | 3/1994 | Mischenko | 604/192 |

FOREIGN PATENT DOCUMENTS

| | | | |
|---|---|---|---|
| 2634651 | 2/1990 | France | 604/192 |
| 1690781 | 11/1991 | U.S.S.R. | 604/264 |
| 970645 | 1/1964 | United Kingdom . | |
| 9113552 | 1/1992 | United Kingdom . | |
| 93003777 | 3/1993 | WIPO | 604/264 |
| 94009840 | 5/1994 | WIPO | 604/192 |

OTHER PUBLICATIONS

Arthur M. Spokojny, M.D. and Timothy A. Sanborn, M.D. "Management of the Arterial Puncture Site", Journal of Interventional Cardiology, vol. 1, No. 2, 1994, pp. 187–193.

C. R. Bard Brochure, "Non–Urological Catheters and Bougies", p. 23.

Primary Examiner—C. Fred Rosenbaum
Assistant Examiner—Manuel Mendez
Attorney, Agent, or Firm—Ware, Fressola, Van Der Sluys & Adolphson

[57] ABSTRACT

An arterial device for introduction into an arterial puncture to reduce bleeding comprises a flexible tapering cannula 11 having external graduations 15 and an optional protective sleeve 17. The cannula 11 has a central lumen 14 through which a guide wire may extend to facilitate insertion. Gradual withdrawal of the cannula 11 enables the arterial wall to relax gradually to close or reduce the original punctures 16, minimizing haemorrhage.

18 Claims, 1 Drawing Sheet

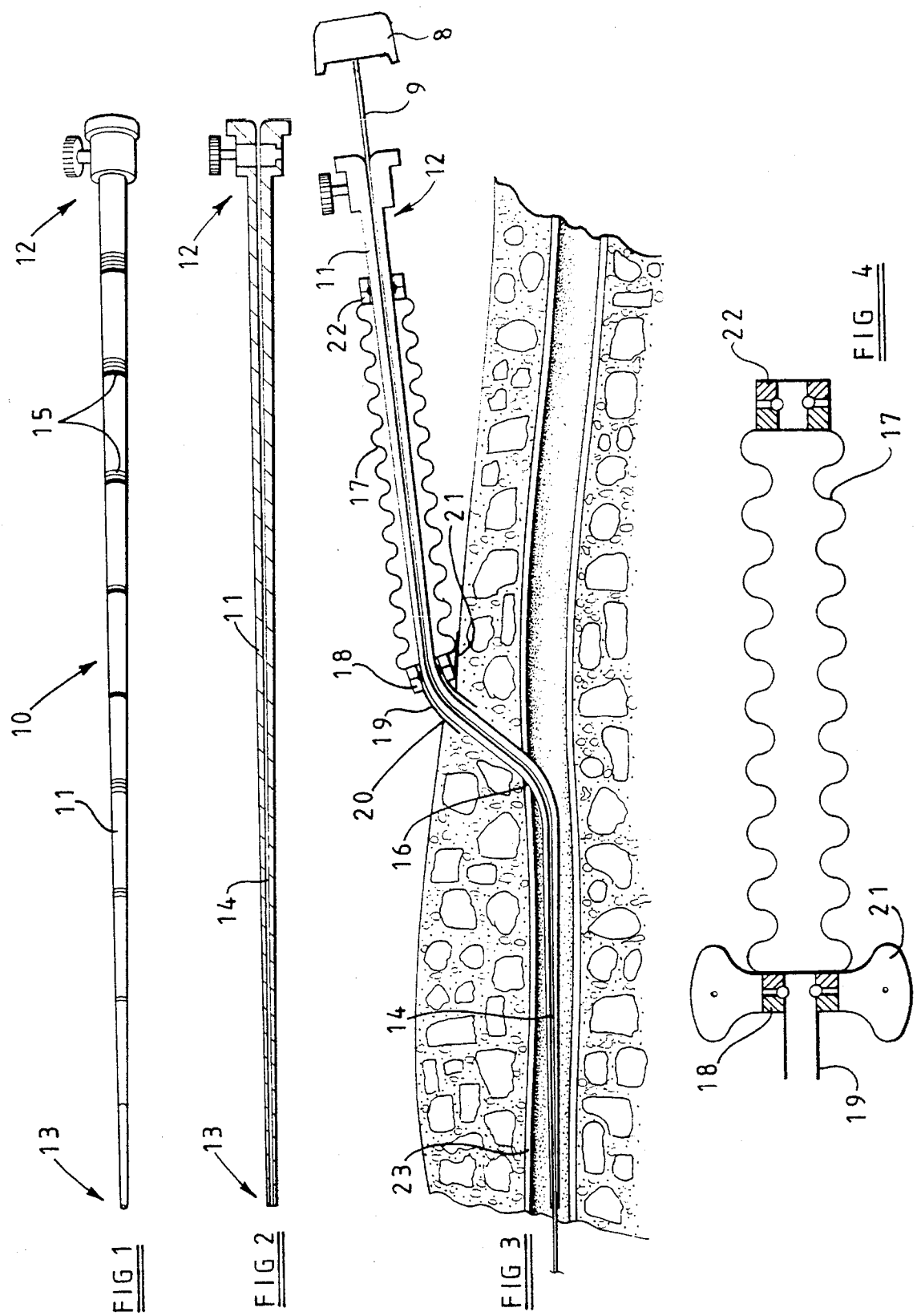

ARTERIAL DEVICE FOR CONTROL OF BLEEDING FROM A PUNCTURE IN AN ARTERY WALL

CROSS REFERENCE TO RELATED APPLICATION

This application is a Continuation-in-Part of application Ser. No. 07/989,053 filed Dec. 10, 1992 now abandoned.

BACKGROUND OF THE INVENTION

1. Field of the Invention

This invention relates to an arterial device and method for control of bleeding from a puncture in an artery which is primarily for use in intensive therapy and interventional cardiology but which may have other medical or surgical application.

To gain access to an artery, the arterial wall must be penetrated. The opening in the arterial wall may initially be quite large, to enable the passage of for example a guiding catheter for transluminal coronary angioplasty or an intra-aortic balloon pump.

When the procedure requiring access to the artery has been completed, and the large diameter device can be removed, extensive bleeding has been found to occur at the puncture in the artery wall, particularly where, following cannulation with a large diameter device, a thin line needs to be left in place for hours or even days for further access in case of emergencies.

Removal of a large sized cannula therefore currently requires prolonged pressure with associated discomfort and often significant haemorrhage into the surrounding soft tissue. The degree of bruising and trauma is partly related to the size and partly to the duration for which the cannula has been left in situ.

Problems associated with arterial bleeding are highlighted in a review article in the Journal of Interventional Cardiology, Vol. 1, No. 2, 1994, pages 187–193—"Management of the Arterial Puncture Site" by Artur M. Spokojny, M.D. and Timothy A. Sanborn, M.D.

2. Description of the Prior Art

There are no arterial devices known to the applicant which assist the closure of a puncture in the wall of an artery to stem arterial bleeding. Arterial devices have been proposed for other purposes unrelated to the stemming of arterial bleeding by arterial wall puncture closure.

For example, U.S. Pat. No. 4,723,939 to Anaise deals with an arterial device for the complete closure of an arterial lumen in order to preserve organs of a cadaver prior to transplantation. The arterial device of Anaise has external band formations which are encircled and engaged by the arterial wall, completely occluding the bore. The device of Anaise is a cannula made of apparently rigid plastics material. It is sized so as to block the artery into which it is inserted.

U.S. Pat. No. 4,738,658 to Magro discloses a cannula device for stemming leakage bleeding from a catheter in situ in an artery. However the cannula device should not penetrate the blood vessel in normal use. It merely seals around the catheter. There is no teaching in Magro as to the control of bleeding from the arterial puncture left by removal of the catheter. This would need to be done by conventional methods such as manual pressing of the arterial puncture site over a prolonged period. Such external compression methods lead to the problems of discomfort, bruising and trauma at the puncture site which are outlined above.

As will be seen from the following description, I propose an arterial device comprising a tapering cannula for the purposes outlined above and for use in the method claimed. Tapering cannulae are known per se for other purposes, including catheterisation of the lung, for example illustrated by the "Thompson Bronchial Catheters" distributed by Bard.

However even the closest prior art known to me is not germane to my invention either as regards the arterial device I propose or the proposed method of use in controlling bleeding from an artery.

SUMMARY OF THE INVENTION

It is an object of the invention to provide an arterial device and method for controlling bleeding from an arterial wall puncture without the prolonged application of external compression.

Viewed from a first aspect the invention provides an arterial device for control of bleeding from a puncture in a wall of an artery having an arterial bore, the arterial device comprising a flexible cannula having an access end and an insertion tip, the external transverse size of the cannula being smaller than the arterial bore and decreasing continuously from the access end to the tip so that the size of the arterial puncture can be matched to said external transverse size with the device partly inserted into the artery and without occlusion of the arterial bore, graduated scale means being provided throughout the tapering length of the cannula, whereby controlled gradual withdrawal of the cannula can occur to permit gradual closure of the arterial puncture, the cannula having a constant circular cross-section internal lumen of a transverse size sufficient to allow passage of a wire.

The transverse size of the internal lumen may be approximately 0.97 mm (0.038 in).

The cannula may be of circular cross-section. It may have an external transverse size of between 1.3 mm to 5 mm (4 French to 15 French) or even larger, and in a preferred form may vary from 1.3 mm to 3 mm (4 French to 9 French).

The cannula may have a length in the range 250 mm to 450 mm. A preferred length is 350 mm.

The proximal access end may have a cap fitting, or alternatively may have a tap.

The arterial device may include a variable length protective sleeve surrounding the cannula towards the proximal access end and the protective sleeve may include anchorage means and/or skin entry means.

The protective sleeve may have clamping valve means at each end thereof, adapted to clamp it in a sealing manner to the external surface of the cannula.

Viewed from a further aspect the invention provides a method of controlling bleeding from an artery having a puncture, the method comprising the steps of inserting an arterial device according to the foregoing statements of invention into the artery by a distance sufficient to match the external diameter of the cannula of the arterial device to the size of the arterial puncture to stop the bleeding; and gradually withdrawing the arterial device from the artery whereby the arterial wall is enabled to relax onto the external surface of the cannula to prevent bleeding throughout said withdrawal.

Withdrawal of the arterial device may be step wise withdrawal by steps each of a predetermined distance as measured on said graduated scale means.

Each withdrawal step may correspond to a predetermined time interval.

The arterial device may be partially re-advanced to stop seepage of blood.

BRIEF DESCRIPTION OF THE DRAWINGS

An embodiment of the invention will now be described in more detail by way of example only with reference to the accompanying drawings in which FIG. 1 is a side elevational view of an arterial device embodying the invention, FIG. 2 is a cross-sectional view of the device, FIG. 3 shows the device in use, FIG. 4 is a sectional view of a sleeve for use with the device.

DETAILED DESCRIPTION OF THE PREFERRED EMBODIMENT

Referring to the drawings, an arterial device generally indicated at 10 comprises a tapering flexible cannula 11. This may be made of any suitable material such as polyurethane, which is smooth, flexible and has minimal thrombogenic properties. The cannula has a proximal access end generally indicated at 12 and a distal insertion tip generally indicated at 13. Between the tip 13 and the access end 12, the cannula continuously and gradually increases in external diameter. Reference to FIG. 2 will show that an internal lumen 14 of substantially constant cross-section is provided. The cross-section of the internal lumen is very small, typically sufficient to allow the easy passage of a wire of the standard guide wire diameter 0.97 mm (0.028 in)

The outer diameter of the cannula 11 tapers over substantially the whole length between a diameter of about 1.3 mm (4 French) and a diameter of about 5 mm (15 French), the length of the cannula being in the range 250–450 mm and typically 350 mm. The cannula is shown as having a circular cross-section but might have a non-circular, for example elliptical, cross-section in some circumstances.

A plurality of graduated markings 15 are visible externally of the cannula. These markings may give a direct reading of diameter or may indicate the length along the cannula from the distal insertion tip 13 to the proximal access end 12, or recommended timings for withdrawal of the cannula.

Referring to FIG. 3 of the drawings, an arterial device embodying the invention is shown in use in the method of the invention. An artery 23 has a puncture 16 which has been used for a medical procedure. For example the artery 23 may have had the wall punctured at 16 for the insertion of a balloon catheter or other device used in interventional cardiology. Such a device usually has a guide wire along which the device is threaded and it may be required to leave the guide wire in place in the artery in case further intervention is necessary after withdrawal of the catheter. However otherwise the puncture in the arterial wall needs to be closed up to stem arterial bleeding.

The cannula 11 of the arterial device 10 of the present invention is inserted into the arterial puncture by a distance sufficient to match the external diameter of the cannula 11 to the arterial puncture made by the initial arterial procedure. Insertion is usually facilitated by the presence of a guide wire in the artery 23, around which the cannula is slid.

Before insertion of the cannula 11 into the arterial puncture 16, a transparent concertina plastics sleeve 17, illustrated in FIG. 4, may optionally be loaded over the cannula so as to surround it as shown in FIG. 3.

The cannula 11 is inserted into the artery 23 so that the arterial puncture 16 is effectively stoppered by insertion of the cannula. It will be appreciated that the cannula does not occlude the arterial bore. The cannula tip of flexible plastics material lies within the arterial bore and normal arterial blood flow continues around it. However the body of the cannula blocks the puncture site in the arterial wall so that no substantial quantity of blood issues from the arterial wall. Thus, the cannula does not interfere with normal arterial flow but stems external bleeding. The sleeve 17 is slid to a position in which a terminal collar 18 having a short flexible sleeve 19 can be inserted in the skin wound 20 and lightly sutured in place to the skin using the wings 21. Alternatively, it may be taped in place. The other end of the sleeve 17 has a further collar 22 which takes up a position closer to the proximal access end 12 of the cannula 11. The collars 18, 22 are fitted with clamping valves which, once the device 10 is in position, can be tightened to hold the sleeve 17 to the cannula 11 in airtight sealed manner. The clamping valves can be seen in FIG. 4.

It will be appreciated that an access "wire" 9 which may be of metal or other material, will normally be in position within the lumen 14, having been used to facilitate insertion of the cannula 11 and being left in position in the artery for a required period to permit further access in the case of emergencies. The wire may be freely slidable within the cannula 11 or alternatively may be attached by screw means or by being mounted on a standard Luer lock cap 8. One advantage of leaving the wire in situ is that, even if some clotting occurs, this cannot completely occlude the blood vessel, reducing or eliminating the need for flushing.

The arterial device 10 is used to permit controlled closure of the arterial puncture by being withdrawn at a gradual rate, which can be judged from the markings 15 at the skin wound 20. These may indicate diameter, length measured from the insertion tip or suggested withdrawal timings.

The arterial wall is enabled to relax onto the external surface of the cannula 11 at a particular point along its length and gradual withdrawal of the tapering cannula permits its eventual removal without the need for considerable pressure to be exerted at the site of the arterial puncture to prevent haemorrhage. If excessive bleeding or seepage of blood occurs during controlled withdrawal, it may be stopped by slight advance of the cannula further into the artery. The presence of the sleeve 17 retains the sterility of the withdrawn and reinserted portion of the cannula in the case of such reinsertion.

The rate of withdrawal can be varied depending on the initial size of the arterial puncture 16 and the patient's characteristics and is also dictated by the clinical need for maintaining arterial access, in some circumstances. Where further access to the artery will or may be needed, the insertion tip can be left in position to avoid the need for a further incision. However, the guide wire can usually be removed.

At a specified time decided by the clinician, the arterial device 10 can be completely removed. At this stage only the thin tip portion 13 of the device remains in the artery and complete removal will be accompanied by only minor bleeding, which can readily be controlled by appropriate hand pressure or by a pressure bandage.

The proximal access end 12 of the cannula is provided with a closable one-way or multi-way tap or with a standard Luer lock end cap or other appropriate fitment. A tap may be useful if a saline infusion may be needed. The transparent variable length sleeve 17 may be omitted, although it provides a useful means of maintaining the sterility of the external surface should it become necessary to reinsert the arterial device as described.

It is necessary to select the sizes of the arterial device such as to permit its use in the method described. Although the maximum diameter of the cannula may approach that of the arterial lumen, at no time is the lumen itself to be blocked by the cannula. The size of the puncture is what determines the maximum size of the cannula and it is therefore preferred that the external transfer size of the cannula will vary in normal use from 4 French to 9 French (1.3 mm to 3 mm) although the maximum size may go up to 15 French (5 mm) or even larger.

The material of the catheter must be very flexible because it has to lie within the artery which will vary in features such as position and curvature from one patient to another or at different sites in the same patient. Stiff and particular rigid plastics must be ruled out as potential materials. Similarly, no external formations may be provided on the cannula because these would interfere with the smooth withdrawal of the cannula and also might encourage coagulation of blood on the cannula during use. The plastics material must have minimal thrombogenic properties. Finally, the taper must be smooth and continuous throughout the length of the cannula since any change in the rate of taper or step formations would reduce the effectiveness in the method of the invention.

I claim:

1. An arterial treatment device for control of bleeding from a wall of an artery having an internal arterial bore, with a first known cross-sectional area, through a surgical puncture incision penetrating said wall and having a second known cross-sectional area substantially smaller than said first area, the device comprising:

a flexible tapered tubular cannula having a larger proximal access end and a smaller distal insertion tip, the maximum external cross-sectional area of the cannula at said access end being substantially smaller than the internal cross-sectional area of the arterial bore at said puncture incision, the external cross-sectional area of the cannula decreasing continuously from the access end to the insertion tip, the cannula having a constant circular cross-section internal lumen of a diameter sufficient to allow telescoping passage of a guide wire, and graduated scale indicia being provided throughout the overall length of the tapered cannula, whereby insertion of the flexible tapered cannula's insertion tip through the puncture incision in the arterial wall and partial lengthwise telescoping insertion of the tapered cannula to move the tip along the interior bore of the artery away from the puncture incision allows the surgeon to continue said telescoping insertion until the time is reached when the tapered cannula's external cross-sectional area matches the cross-sectional area of the surgical puncture incision, stanching bleeding therefrom without occluding the arterial bore, and whereby controlled gradual withdrawal of the cannular can follow in intermittent stages guided by the graduated scale indicia, achieving gradual relaxing closure of the arterial puncture incision while minimizing bleeding.

2. Arterial device according to claim 1 wherein the internal lumen has a transverse size of 0.97 mm (0.038 in).

3. Arterial device according to claim 1 wherein the cannula is of circular cross-section.

4. Arterial device according to claim 1 wherein the external transverse size of the cannula is in the range 1.3 mm to 5 mm (4 French to 15 French).

5. Arterial device according to claim 4 wherein the external transverse size of the cannula is in a range from 1.3 mm to 3 mm (4 French to 9 French).

6. Arterial device according to claim 1 wherein the cannula has a length in the range 250 mm to 450 mm.

7. Arterial device according to claim 6 wherein the cannula has a length of approximately 350 mm.

8. Arterial device according to claim 1 wherein the access end is provided with a closable infusion tap opening into the cannula's internal lumen and having a manually actuated closure, whereby liquid medication can be delivered to the artery therethrough.

9. Arterial device according to claim 1 wherein the cannula's access end is provided with a Luer lock closable cap fitting engageable with the cannula to close the access end of the cannula's internal lumen.

10. In combination, a guide wire and an arterial device according to claim 9 wherein the access end of the guide wire is anchored to the cap fitting at the location thereon abuttingly juxtaposed to the access end of the cannula's internal lumen when the cap is closed on the cannula.

11. In combination, the arterial device according to claim 1, further including a variable length protective sleeve surrounding and enclosing the external surface of the cannula, and extending from a central point along its length towards a point closely adjacent to the access end of the cannula.

12. The combination according to claim 11 wherein the protective sleeve includes terminal collar anchorage means encircling the sleeve at it distal end and provided with clamping means for gripping the cannula at said central point to form an airtight, sealed connection and also provided with laterally extending wings for securing said terminal collar to the skin of a patient.

13. The combination according to claim 11 wherein the protective sleeve includes skin entry means.

14. The combination according to claim 11 wherein the protective sleeve has clamping valve means at each end thereof, conforming in a sealing manner to the external surface of the cannula, whereby it is clamped to the cannula in use.

15. A method of controlling bleeding from an arterial bore inside an artery, having a first known cross sectional-area, through a surgical arterial wall puncture incision, having a second known cross-sectional area substantially smaller than said first area, comprising the steps of providing a flexible tapered tubular cannula having an external cross-sectional area decreasing continuously from a larger proximal access end to a smaller distal insertion tip, the maximum external cross-sectional area at said proximal access end being larger than said second incision area and substantially smaller than said first arterial bore area, said cannula having graduated scale indicia displayed throughout the continuously diminishing tapered overall length of said cannula, inserting the insertion tip of said flexible tapered cannula through said incision into said arterial bore, telescopingly advancing the flexible cannula through the incision, moving its insertion tip along the arterial bore away from said incision, continuing said advancing movement until the external cross-sectional area of the flexible tapered cannula at the cannula region entering said incision substantially matches said second incision cross-sectional area, substantially stopping bleeding through said incision, and gradually withdrawing the cannula from said incision over a period of time, whereby gradually relaxing closure of the surgical incision encircling the external surface of the cannula minimizes bleeding through said incision throughout said gradual withdrawal period.

16. A method according to claim 15 wherein the arterial cannula is withdrawn step wise by steps each of a predetermined distance as measured on said graduated scale indicia.

17. A method according to claim 16 wherein each withdrawal step corresponds to a predetermined time interval.

18. A method according to claim 20 wherein the arterial cannula is partially re-advanced into the artery to stop seepage of blood.

* * * * *

UNITED STATES PATENT AND TRADEMARK OFFICE
CERTIFICATE OF CORRECTION

PATENT NO. : 5,478,326
DATED : Dec. 26, 1995
INVENTOR(S) : Man F. Shiu

It is certified that error appears in the above-indentified patent and that said Letters Patent is hereby corrected as shown below:

Column 6, Claim 12, Line 37, after "connection"

insert -- , --

Column 8, Claim 18, Line 7, change "20" to --15--

Signed and Sealed this

Twenty-fifth Day of June, 1996

Attest:

BRUCE LEHMAN

Attesting Officer      *Commissioner of Patents and Trademarks*